US00RE34021E

United States Patent [19]

Mueller et al.

[11] E Patent Number: Re. 34,021

[45] Reissued Date of Patent: Aug. 4, 1992

[54] PERCUTANEOUS FIXATION OF HOLLOW ORGANS

[75] Inventors: Peter R. Mueller, Lexington; Alan S. Brown, Longmeadow; Marc J. Tolkoff, Brookline, all of Mass.; Frank B. Crawford, New Boston, N.H.

[73] Assignee: Abbott Laboratories, Abbott Park, Ill.

[21] Appl. No.: 435,343

[22] Filed: Nov. 13, 1989

Related U.S. Patent Documents

Reissue of:

[64] Patent No.: 4,705,040
Issued: Nov. 10, 1987
Appl. No.: 798,781
Filed: Nov. 18, 1985

[51] Int. Cl.[5] ..... A61M 31/00

[52] U.S. Cl. ..... 604/51; 604/280; 606/108

[58] Field of Search ..... 604/51, 52, 53, 280, 604/281, 282, 283, 264, 272; 606/108, 215, 220

[56] References Cited

U.S. PATENT DOCUMENTS

| | | | |
|---|---|---|---|
| 487,304 | 12/1892 | Todd . | |
| 1,059,631 | 4/1913 | Popovics . | |
| 3,039,468 | 6/1962 | Price | 128/347 |
| 3,103,606 | 9/1963 | Bone . | |
| 3,209,422 | 10/1965 | Dritz . | |
| 3,332,118 | 7/1967 | Temple . | |
| 3,470,875 | 10/1969 | Johnson . | |
| 3,521,640 | 7/1970 | Carey et al. | 128/334 |
| 3,527,223 | 9/1970 | Shein . | |
| 3,540,451 | 11/1970 | Zeman . | |
| 3,589,355 | 6/1971 | Lee | 606/108 X |
| 3,598,124 | 8/1971 | Anderson | 128/275 |
| 3,643,649 | 2/1972 | Amato . | |
| 3,656,479 | 4/1972 | Huggins | 128/214.4 |
| 3,675,639 | 7/1972 | Cimber | 606/108 X |
| 3,820,535 | 6/1974 | Marco | 128/839 |
| 3,835,863 | 9/1974 | Goldberg | 128/350 R |
| 3,910,281 | 10/1975 | Kletschka et al. . | |
| 3,920,023 | 11/1975 | Dye et al. | 128/347 |
| 4,006,747 | 2/1977 | Kronenthal et al. . | |
| 4,037,600 | 7/1977 | Poncy et al. | 128/214.4 |
| 4,054,136 | 10/1977 | von Zeppelin | 128/214.4 |
| 4,077,412 | 3/1978 | Moossun | 128/347 |
| 4,103,690 | 8/1978 | Harris . | |
| 4,160,453 | 7/1979 | Miller . | |
| 4,235,238 | 11/1980 | Ogui et al. . | |
| 4,393,873 | 7/1983 | Nawash et al. | 604/151 |
| 4,405,314 | 9/1983 | Cope | 604/51 |
| 4,440,171 | 4/1984 | Nomoto et al. . | |
| 4,471,782 | 9/1984 | Shuffield . | |
| 4,483,562 | 11/1984 | Schoolman . | |
| 4,534,363 | 8/1985 | Gold | 128/772 |
| 4,669,473 | 6/1987 | Richards et al. | 606/215 |

FOREIGN PATENT DOCUMENTS

| | | |
|---|---|---|
| 2157529 | 5/1973 | Fed. Rep. of Germany . |
| 2438464 | 6/1980 | France . |
| 401677 | 11/1933 | United Kingdom . |

OTHER PUBLICATIONS

Cope, "Suture Anchor for Visceral Drainage", *AJR*, vol. 146, Jan. 1986, pp. 160–161.

Gauderer and Ponsky, "A Simplified Technique for Constructing a Tube Feeding Gastrostomy", *Surgery, Gynecology & Obsterics*, Jan. 1981, vol. 152, pp. 83–85.

Russell, Brotman and Norris, "Percutaneous Gastrostomy", *The American Journal of Surgery*, Jul. 1984, vol. 148, pp. 132–137.

*Primary Examiner*—John D. Yasko
*Attorney, Agent, or Firm*—Fish & Richardson

[57] ABSTRACT

For percutaneous fixation of a hollow organ of a body, a hollow needle carrying a retaining device attached to a tension filament through the skin into the hollow organ, the retaining device is released from the needle, and the organ is fixed by adjusting the tension on the filament and clamping the filament outside the body by means bearing upon the exterior of the body.

19 Claims, 4 Drawing Sheets

PERCUTANEOUS FIXATION OF HOLLOW ORGANS

Matter enclosed in heavy brackets [ ] appears in the original patent but forms no part of this reissue specification; matter printed in italics indicates the additions made by reissue.

*This application is a reissue of Ser. No. 06/798,781 filed Nov. 18, 1985, U.S. Pat. No. 4,705,040.*

In preparation for inserting a tube such as drainage or feeding tube into a hollow organ of the body, it is desired to fix the hollow organ to a body wall. This aids in accurate placement of the tube and in preventing leakage that can contaminate the peritoneal cavity and lead to peritonitus.

In the past, fixation of hollow organs has mainly been accomplished by suturing during open surgery as part of the procedure of placing the tube. However, to avoid the drawbacks of incision, general anesthesia and need for an operating room, it is desirable to accomplish the entire procedure without surgery.

For this purpose, a technique has been used which obtains some degree of fixation, particularly of the gastric wall to the body wall. A tube with a blunt end which is installed, in a retrograde manner from the inside of the stomach towards the outside, the blunt end of the tube engaging the stomach wall and holding it in place. For this purpose, a gastroscope is placed in the patient's stomach, a site is chosen on the skin using the light from the gastroscope, a puncture is made through the skin and a guidewire is introduced into the stomach. This guidewire is grasped by the gastroscope and pulled out of the stomach through the esophagus and out of the mouth. The end of the wire protruding from the mouth is then attached to a tube, having a leading pointed end and a trailing blunt end. The guidewire is pulled back into the stomach and the pointed end of the tube is pulled through the gastric wall and the skin until the blunt end of the tube is secured against the stomach and holds the stomach wall against the body wall.

The disadvantages of this technique are that it requires a big gastroscope which has inherent risks, it is not possible to employ a gastroscope with all patients, and the tube is critically dependent upon its own fixation. If such tube were removed inadvertently, the fixation would be lost, leaving an open hole in the stomach and no method of fixation, with resultant leak into the peritoneal cavity.

Also in the prior art, but not to be confused with techniques which achieve secure fixation of the wall of the hollow organ to the body wall, are the uses of tubes which have ends of various designs to prevent inadvertent withdrawal of the tube itself. There are several of these, some of which are introduced percutaneously while others are utilized during surgical procedures. One is known by the name Mallincott, another is a balloon employed on the end of a Foley catheter, and there are various looped catheters such as the Cope loop. Basically, the ends of these catheters prevent the catheter from being withdrawn and to some degree may serve to retain the hollow organ in position against the body wall. However, in order to fix a hollow organ wall in place one has to apply traction, but traction on the catheter tends, after a period of time, to pull the catheter out, and therefore the needed degree of traction, for secure fixation, is incompatible with the primary objective of such devices.

Objects of the present invention are to provide a device and method to obtain better fixation of hollow organs by techniques that do not require surgery.

SUMMARY OF THE INVENTION

According to the present invention, the task of fixation or anchoring of the hollow organ is separated from that of catheterization for drainage or infusion, and fixation is achieved by percutaneous placement of tack devices.

According to the invention, a series of spaced apart tacks or retention devices are introduced percutaneously to the inside of the hollow organ, each associated with a filament-like tension piece which is used to apply fixation force, outside of the body by a device that bears against the exterior of the body. Preferably, the introduction is achieved by placing a stiff T-shaped end of a tension filament within the lumen of a needle and allowing the flexible filament to protrude from a small slot at the tip of the needle, with the filament trailing alongside during introduction. After the needle is passed through the skin and enters the hollow organ, a stylette or obturator is used to dislodge the head of the T piece from the lumen and the needle can be withdrawn. At this point tension is applied along the filament and the "T" head is urged snugly against the inside surface of the hollow organ and holds it there. In practice, four needles may be employed to place four separate T-shaped devices. Preferably, the head of the T element is of the order of a centimeter long and the filament is approximately 10 to 15 centimeters long. In the case of the stomach, four of these tack devices are placed at the corners of a one or two-inch square and then the feeding tube is placed in the center of this square.

The head of the T is preferably an elongated cylinder, at the mid portion of which is attached a filament of synthetic resin, the head being small enough to be introduced percutaneously and sufficiently stiff to prevent bending of the head so that it does not bend and pull out, and the filament being strong in tension and flexible enough to bend approximately 90° at its junction with the head of the T piece. In the presently preferred form, the head of the T element is aligned with the axis of the needle and housed within it during insertion.

Preferably, the needle comprises conventional hypodermic tubing, 16 gauge, regular or thin wall, the needle has a single bevel and the slot is cut from the more proximal surface of the bevel, and extends back, approximately ¾ of a centimeter in length, sufficient to expose the point of attachment of the filament when the head of the T element is entirely housed within the needle. Before use of the needle, usually a small puncture with a hemostat is made in the skin to free the subcutaneous tissues, without penetrating the organ. The needle is then used to make the initial puncture into the organ. At the time of the initial puncture, the organ is not fixed at all, so it is important that the needle be quite pointed, e.g. beveled about 30°.

By having the needle hollow throughout its length, a stylette or obturator can pass down the lumen to dislodge the T after it is in place, and during introduction, the hollow lumen is utilized to aspirate air from the stomach to prove the location of the needle tip.

In preferred embodiments, a sterile kit is provided to the physician comprising the percutaneous insertion needle, the "T" element, with head preloaded in the needle, and with the filament lying alongside. An appropriate assembly of devices is pre-arranged along the filament for applying traction and securing the "T" element in place, preferably comprising a compressible pledgette to bear against the body, a compression-applying retention disc to bear against the pledgette and a crimpable clamping element for permanently clamping the filament and applying compression to the compression disc.

The method of the invention for the percutaneous fixation of organs is characterized by the steps of inserting a hollow needle carrying a retaining device attached to a filament, through the skin into the organ, releasing the retaining device from the needle, and fixing the organ by adjusting the tension on the filament and clamping the filament by means bearing on the exterior of the body.

In preferred embodiments of this method, the retaining device comprises a head that extends cross-wise to the filament in a "T" arrangement and a second filament is secured to one end of the head such that the head can be removed from the organ by pulling on the second filament while releasing the first filament.

In preferred embodiments of manufacture of the percutaneous fixation device, the device comprises a hollow tubular head and a tension filament, the method comprising: drilling a hole in the side of the tubular head, introducing thermoplastic resin, e.g. a second filament, into the tubular head, melting the resin within the head, fusing the melted second filament to the first filament by passing the first filament through the side hole so that it contacts the melted resin, and allowing the device to cool.

A preferred embodiment of the percutaneous fixation device comprises: a slotted hollow needle, a "T" head element attached to a filament, the filament being attached to the mid-portion of the head. The head is preloaded within the slotted needle such that the filament passes through the slot of the slotted needle, and a set of exterior tension applying devices are prearranged along the length of the filament. In another embodiment, a second filament is attached to one end of the head, adapted to withdraw it by releasing the first filament.

DESCRIPTION OF PREFERRED EMBODIMENTS

The drawings will first briefly be described.

Figures 3, 3A, 3B, 3C:
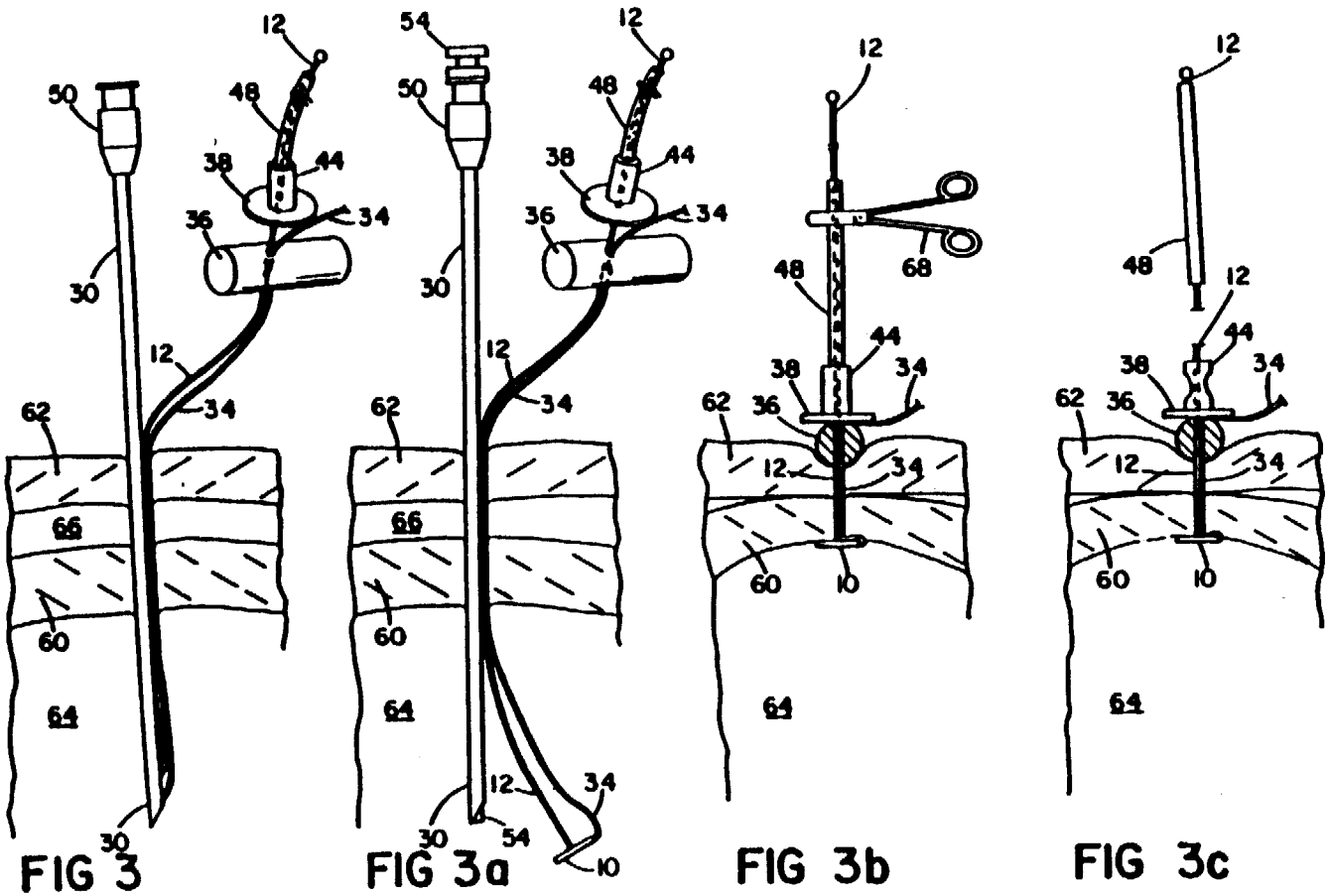
Figure 4:
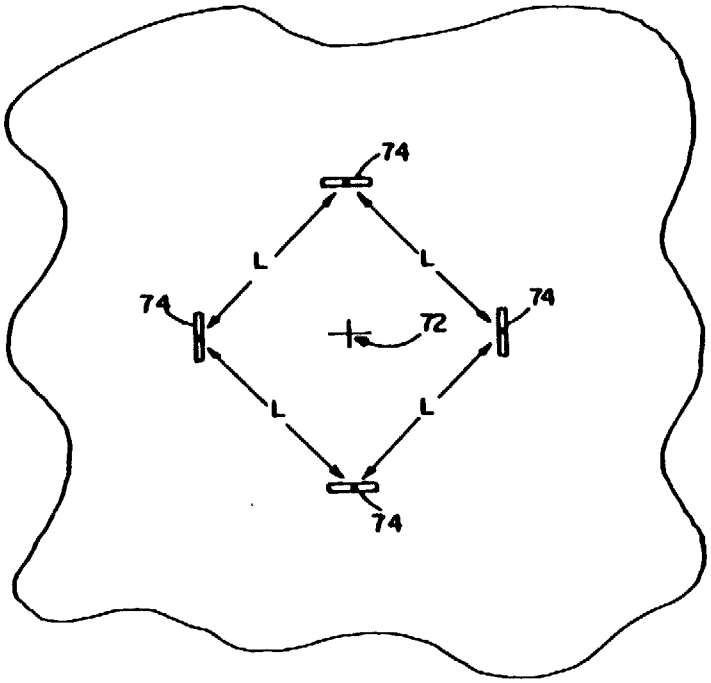
Figure 3D:
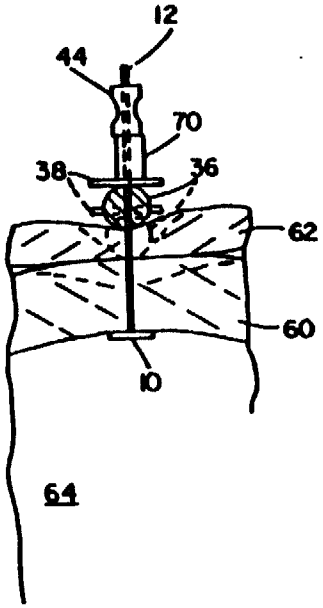

FIG. 3—3(c) are diagrammatic representations to illustrate steps taken during the insertion of a "T" element and subsequent manipulations for securing the "T" element in place to fix the stomach to the abdominal wall;

FIG. 3(d) is a view similar to FIG. 3(c) of an alternative embodiment;

FIG. 4 is a diagrammatic representation of the positioning of four tacks according to the invention, securing the stomach to the abdominal wall in preparation for insertion of a feeding catheter through the abdominal wall.

STRUCTURE

Percutaneous fixation device

(a) "T" element

Figure 1:
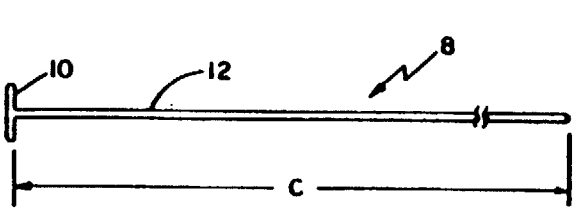
FIG. 1 is a side view of a "T" element for use in the percutaneous fixation device according to the invention.
Figure 1A:
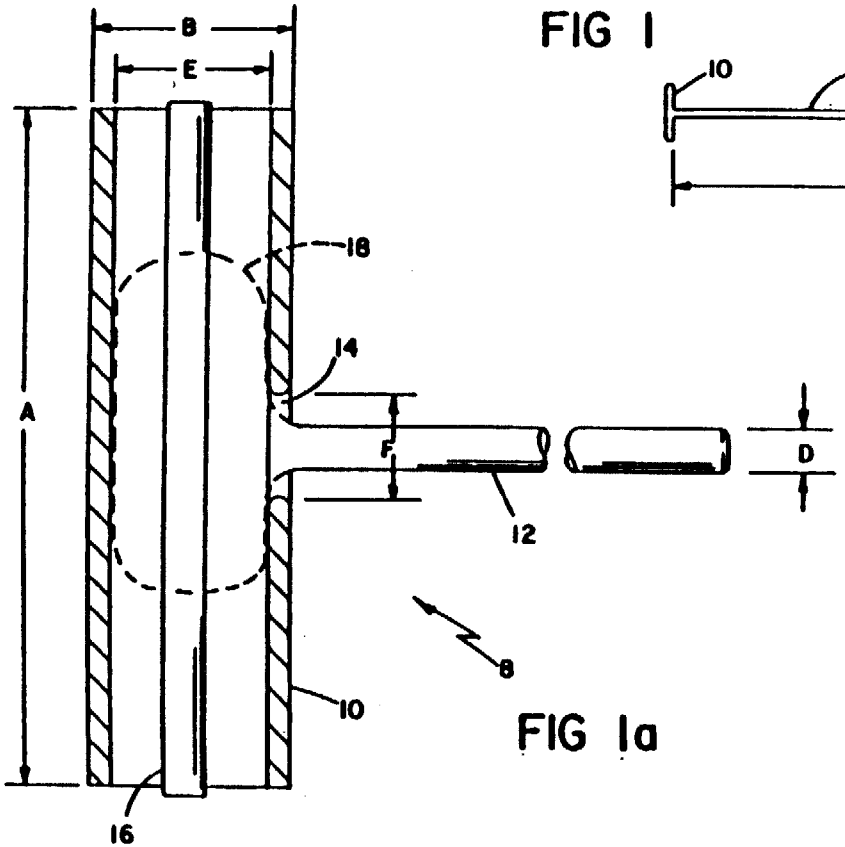
FIG. 1(a) is a sectional view of highly enlarged scale through the "T" element of FIG. 1.

Referring to FIGS. 1 and 1(a) the "T" element 8 consists of head 10 and filamentary tension leg 12. In this embodiment, head 10 preferably has length A, ¼ inch, outer diameter B, 0.035 inch and rounded ends, and filament 12 has length C, 5 inch, and outer diameter D, 0.008 inch and is highly flexible. The head is constructed to resist bending when pulled by attached filament 12 and is radiopaque so that it can be seen with a fluoroscope during and after insertion into the body.

In this embodiment the head is of stiff stainless steel tubing with internal diameter E, 0.025 inch and with a central hole 14 formed in its side of diameter F, 0.020 inch. Filament 12 is attached to head 10 by inserting a separate segment of filament 16 within and axially aligned with head 10, heating the head to melt segment 16 with the result that the resinous filament melts and draws into the form of a large central ball 18, and pushing filament 12 through hole 14 into the molten ball 18. When cooled and set, ball 18 is substantially larger than central hole 14 and forms a firm root for filament 12, attaching it to head 10. Attachment of filament 12 to ball 18 also prevents the edges of the filament from touching the portions of the tube that bound hole 14, to avoid abrasion and subsequent breakage of filament 12. Also, the gradually enlarging transition region from filament to ball serves as a strain relief. Filament 12 is preferably of nylon material such as suture material or fishing line, or of similar polymers, such as polyester. Inner ball 18 may be of any compatible, strong material but preferably is of the same thermoplastic material as that of filament 12 to ensure good bonding, to form a strong, integrated structure.

(b) Percutaneous introductory device

Figure 2:
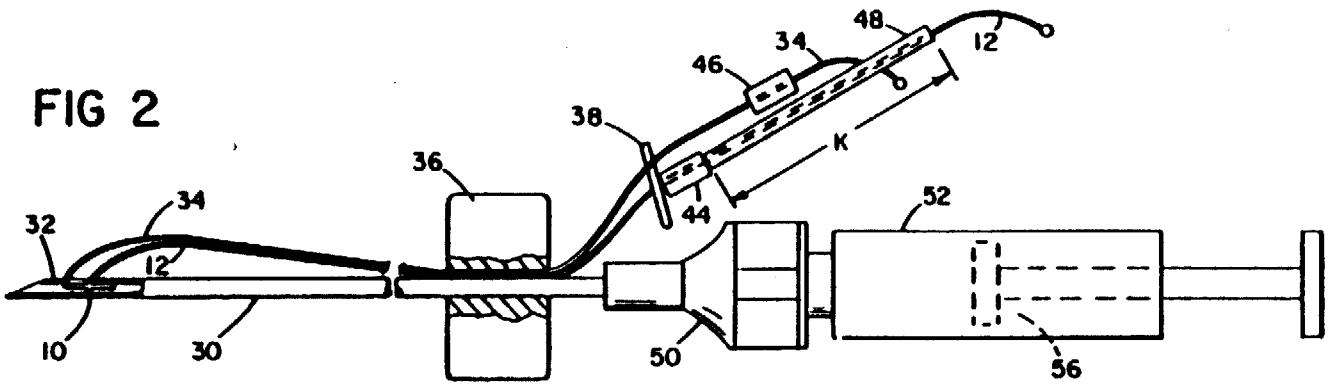
FIG. 2 is a side view of a preloaded needle assembly for percutaneous insertion of the "T" element into the body to fix the position of an organ.
Figure 2A:
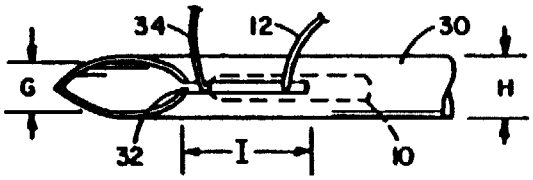
FIG. 2(a) is a plan view of enlarged scale of the needle tip region of the assembly of FIG. 2.

Referring to FIG. 2(a), head 10 of the "T" element is inserted into the tip of hollow insertion needle 30 which has a longitudinal slot of approximate length I, 0.3 inch in its tubular wall. Filament 12 passes through slot 32 and bends back in the proximal direction. In one embodiment a second filament 34 is attached to one end of head 10. This second filament is provided as a means for removing the head of an inserted "T" element from the body after use (see below). Preferably filament 34 is of material similar to filament 12 and is attached to head 10, through a hollow end of the head, at the same time as filament 12 is attached, when ball 18 is molten.

Needle 30 has a sharp tip, a length suitable to permit percutaneous insertion (e.g. 5 inches for stomach tack purposes) and an internal diameter G great enough to accept head 10 so that head 10 is entirely within the needle when the needle is thrust through the flesh and the organ wall. Preferably needle 30 is 16 gauge, small enough in external diameter H that it can be percutaneously introduced and penetrate the skin and flesh of the patient and the wall of the desired hollow organ (e.g. the stomach) without bending.

Referring to FIG. 2 the two filaments 12 and 34 and needle 30 are inserted through compressible pledgette 36 such that the filaments run alongside the exterior of the needle. Pledgette 36 is preferably of a soft, absorbent, spongy material such as cotton or methylcellulose, and acts as a cushion against the skin and as an absorbent for fluids. The filaments also ass through retention washer 38, and crimpable clamp devices 44 and 46. Filament 12 also passes through plastic tube 48 which acts as a temporary clamping site (see below). (In another embodiment, FIG. 3d, filament 12 passes through a second crimpable clamp device 70, between device 44 and retention washer 38, which can be used to reset the device should it loosen over time after device 44 has been initially clamped). Washer 38 is of material such as acrylic or a similar plastic or of metal, of approximate thickness 0.060", sufficiently stiff to transmit retention stresses between filament and pledgette. Plastic tube 48 must be of a material which satisfies two different requirements, (i) sufficiently supple in the direction of its diameter so that it can be squeezed by a clamp to grip the filament within it, and (ii) strong in compression to temporarily axially bear upon device 44 and via device 44, upon the pledgette, to apply tension and fix "T" element 8 in place. For example, tube 48 may be of polyethylene, vinyl, or other flexible polymer tubing of suitable wall thickness. Tube 48 is of length K, approximately 1 inch. Crimp rings 44, 46, and 70, are preferably of aluminum so that they are readily fixed in place using common medical instruments that apply clamping pressure (e.g., a hemostatic clamp).

Figure 2B:
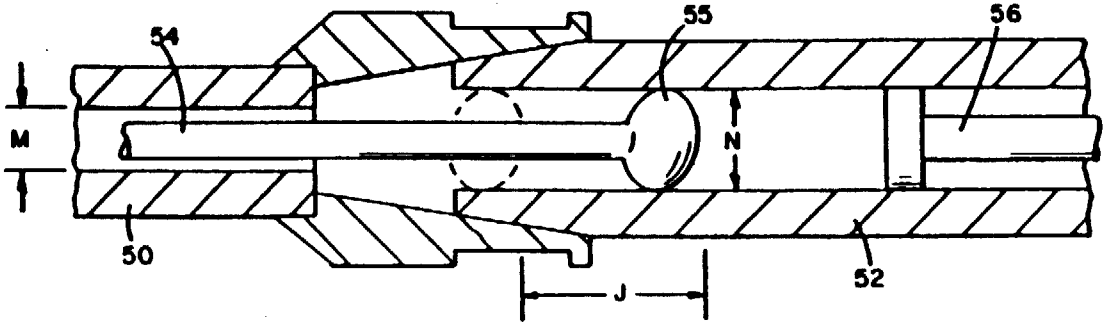
FIG. 2(b) is a longitudinal sectional view of enlarged scale through the hub region of the needle of FIG. 2.

Referring to FIG. 2, needle 30 ends at a leur lock fitting at hub 50, into which syringe 52 with plunger 56 may be inserted. Referring to FIG. 2b, obturator or stylette 54 is placed within needle 30 with one end near to or touching head 10 of the "T" element 8, and the other end extending through hub 50. The proximal end 55 of obturator 54 is of sufficient width, N, greater than the internal diameter, M, of needle 30, that it is unable to pass through needle 30, so that it serves as a stop. Obturator 54 is of sufficient length to extend from the distal end of needle 30 approximately 1 inch into syringe 52. When plunger 56 of syringe 52 is pushed fully down it can engage the proximal end of obturator 54 and eject head 10 from the distal end of needle 30, by moving obturator 54 distance J, approximately the length of head 10 plus any distance provided between the tip of the needle and head 10. (If desired obturator 54 may instead by moved distance J by pushing it with a finger).

METHOD OF INSERTION

Prior to insertion of the "T" element 8 of the percutaneous fixation device into the stomach according to this embodiment, a nasogastric tube is passed and the patient given intravenous glucogon to temporarily stop the motion of the gastro-intestinal tract and thus make it easier to distend the stomach. An air pumping bulb is then attached to the nasogastric tube and air is carefully pumped into the stomach. When the stomach is moderately distended, site 72 (FIG. 4) is chosen, at which a catheter is to be inserted through the skin and an area of approximately 2 inch square around the site is infiltrated with local anaethesia. The points 74 (FIG. 4) for introduction of the heads of the percutaneous fixation devices (usually four in number) are chosen and marked.

Referring to FIG. 3, needle 30 containing the head 10 of the "T" element 8 is filled with liquid by the syringe and the percutaneous fixation device is inserted through skin and flesh 62, across intraperitoneal space 66 and through stomach wall 60 into the stomach cavity 64. Insertion is followed using a fluoroscope to ensure that needle 30 is correctly positioned. If desired, needle 30 may be filled with an appropriate liquid, such as radiopaque material. If this is done, then the movement of needle 30 into the body is more easily followed with the fluoroscope. When the tip of needle 30 is within the air-containing stomach, by moving the plunger of the syringe proximally, air bubbles will enter needle 30 and the attached syringe. Observance of these air bubbles will aid the inserter in confirming insertion into the stomach cavity (FIG. 3).

Referring to FIG. 3(a), head 10 of the percutaneous fixation device is removed from needle 30 by insertion of obturator 54 into needle hub 50 and gently pushing obturator 54 down distance J (FIG. 2b) until its distal end is next to the distal end of needle 30 (FIG. 3(a). The head 10 may be displaced using the syringe as shown in FIG. 2(b). Once head 10 has been displaced into the stomach space, needle 30 may be removed.

Referring to FIG. 3(b), by pulling on filament 12, head 10, engaged cross-wise upon the stomach wall, can be used to pull stomach wall 60 towards abdominal wall 62 until they touch. Head 10 is then secured by pushing pledgette 36 along filament 12 with washer 38 until the indentation of the skin by the pledgette indicates a safisfactory tension on filament 12. Washer 38 and pledgette 36 are then secured in place temporarily by clamp 68 applied to tube 48.

Referring to FIG. 4, the remaining percutaneous fixation devices 74, are inserted and fixed in a similar manner to the first one and the tension on each of filaments 12 adjusted. Then each is more permanently clamped by crimping the crimpable clamp devices 44 (FIG. 3(c)). (The devices are usually placed distance L, e.g. 1", apart around site 72, the proposed site for insertion of the catheter (FIG. 4).) The parts of the percutaneous fixation device apparatus proximal of the crimped device 46 may then be removed and filament 12 cut to an appropriate length (FIG. 3(c)). Device 44 may be clamped at this point to ensure the availability of filament 34 for utilization at a later time. (see below).

Referring to FIG. 3(d), in an alternative embodiment a second crimpable device 70 may be provided for later adjustment of the tension on filament 12. For example, if the tension slackens, filament 12 may be pulled through crimpable device 70 and then device 70 is fixed to reposition pledgette 36 more inwardly along filament 12, see FIG. 3(d) dotted lines.

REMOVAL OF TACK AND REMAINDER OF PERCUTANEOUS FIXATION DEVICE

Referring to FIGS. 3(c) and (d), the percutaneous fixation devices normally remain in place until the stomach wall and skin have adhered to each other (2–3 weeks). At this point the percutaneous fixation devices may be removed either by cutting filament 12 and allowing head 10 to pass through the intestinal tract of the body or, if filament 34 is present, filament 12 may be cut to release it from clamp 44 or 70 and head 10 may be pulled through the skin using filament 34. Because filament 34 is attached to the end of the head, tension on filament 34 causes the head to turn to align itself with the filament and the exiting opening, thus to facilitate end-wise movement of the head.

MANUFACTURE OF THE PERCUTANEOUS FIXATION DEVICE

Referring to FIG. 1(a) hole 14 of diameter F is drilled into one side of tubular head 10 near to its mid point. Filament 16 of strong thermoplastic is introduced into head 10 and the head is held horizontally with hole 14 pointing upward. The head is then heated in an inert atmosphere (for example nitrogen gas) to a temperature above the melting temperature of filament 16 but below the annealing temperature of the stainless steel of head 10. Using a nylon filament a temperature between 500°-600° F. is suitable. Preferably head 10 is heated using a soldering iron applied to its mid region, on the side opposite of hole 14. When filament 16 has melted, filament 12 of the same material is introduced through hole 16 and pushed into molten ball 18. If to be employed, filament 34 is also inserted at this time throughone end of head 10 and pushed into molten ball 18. The assembly is then permitted to cool.

Once molten ball 18 and the filament are bonded together, pledgette 36, washer 38, tube 48, and clamping devices 44, 46, and 70 are threaded in appropriate order along filaments 12 and 34. Each of these pieces has a hole just greater in diameter than the respective filament, i.e. approximately 0.010". Head 10 is inserted into hollow slotted needle 30 such that filament 12 passes through the slot and the attached end of filament 34 is at the distal end of needle 30. The whole apparatus may be gas sterilized.

USES

The percutaneous fixation device is useful for the fixation or anchoring of hollow organs without the need for a complex operation, or the need to engage a surgeon. Organs such as the stomach, kidney, gall bladder, large and small bowel, urinary bladder, and duodenum may be readily moved within the body to any desired position simply by inserting "T" element 8 of the percutaneous fixation device into the organ and adjusting the tension on attached filament 12. Once fixed in place, catheters are readily inserted into the desired organ. Since the percutaneous fixation device may be readily removed, using filament 34, there is no problem with leaving the head of the percutaneous fixation device within the body, though in certain cases the elimination system of the body may be employed to remove the head, and in still other cases the head may be left permanently in the body.

What is claimed is:

1. A method for the fixation of a hollow organ of a living body to a body wall comprising:

percutaneously inserting a rigid hollow needle carrying a retaining device attached to a trailing tension filament, through the skin, from outside the body, into said hollow organ in the manner that a portion of said trailing tension filament remains outside of the body, said retaining device having a portion adapted to engage and apply pressure to an interior wall of said hollow organ, releasing said retaining device within said hollow organ from said needle, pulling a portion of said trailing tension filament from outside the body to draw said retaining device against the interior wall of said hollow organ to pull said organ against the body wall, and fixing said organ by adjusting the tension on said filament and clamping said filament outside the body by means bearing upon the exterior of the body.

2. The method of claim 1 wherein said retaining device comprises a head that extends cross-wise to said filament in a "T" arrangement upon release from said needle.

3. A percutaneous fixation device suitable to fix the position of a hollow organ within a body which comprises:

a hollow needle; and a "T" head, wherein said head comprises a stiff hollow tube having a hole in its side, a root mass of resinous material larger than said hole disposed within said tube, a tension filament attached to the mid-portion of said head, said head dislodgedly held within said needle, said filament extending through said hole and bonded to said mass, with said filament extending back with said needle, and means threaded on said filament for bearing with compression against the body to apply tension to said filament to draw said head against the inner surface of said hollow organ.

4. A retaining element adapted for insertion by a needle and eventual removal through the passage formed by said needle, comprising an elongated stiff head, a primary flexible tension filament secured to said head, and a secondary tension filament secured to an end of said head, adapted to be pulled upon to withdraw said head end-wise upon release of tension on said first tension element.

*5. A percutaneous fixation device suitable to fix the position of a hollow organ within a body, comprising:*

*a "T" head comprising a stiff member,*

*an elongated, relatively more flexible primary tension filament secured at the mid-region of said head, said elongated primary tension filament having a free end trailing back from said head, and*

*compressible means threaded on said elongated primary tension filament for bearing in a cushioning manner with compression against the skin of the body, and means for pressing upon said compressible means while clamping said primary tension member to apply tension to said primary tension filament to draw said head against the inner surface of the hollow organ.*

*6. The primary fixation device of claim 5 wherein said device is adapted for insertion through a passage, and further comprises a secondary tension filament secured at an end of said head, adapted to be pulled upon to withdraw said head endwise upon release of tension on said primary tension filament.*

*7. The percutaneous fixation device of claim 5 or 6 wherein said head comprises a hollow tube having a hole defined in its side wall, and said primary tension filament extends through said hole.*

*8. The percutaneous fixation device of claim 5 or 6 wherein said head comprises a stainless steel tube having a hole defined in its side wall, and said primary tension filament extends through said hole.*

*9. The percutaneous fixation device of claim 5 or 6 wherein said compressible means comprises a compressible cushioning element and a retention member.*

*10. The percutaneous fixation device of claim 9 wherein said compressible cushioning element comprises an absorbent for fluids.*

*11. The percutaneous fixation device of claim 5 or 6 wherein said means for pressing upon said compressible means comprises:*

*a crimpable element in a first state adapted for sliding movement along said primary tension filament, toward said head, in a manner for application of compressive force upon said compressible cushioning element, and in a second state adapted for engage-*

*ment upon said primary tension filament for maintaining said compressible cushioning element in a compressive state, and*

*a clamping element in a first state adapted for sliding movement along said primary tension filament, toward said head, in a manner for application of compressive force upon said compressible cushioning element, and in a second state adapted upon application of radially directed force upon said clamping element for engagement upon said primary tension filament for maintaining said compressible cushioning element in a compressive state.*

*12. A method for the fixation of a hollow organ of a living body to a body wall comprising:*

*inserting a retaining device attached to a trailing tension filament, through the skin, from outside the body, into the hollow organ in the manner that a portion of said trailing tension filament remains outside of the body,*

*said retaining device having a portion adapted to engage and apply pressure to an interior wall of the hollow organ,*

*releasing said retaining device within said hollow organ,*

*pulling a portion of said trailing filament from outside the body to draw said retaining device against the interior wall of the hollow organ to pull the hollow organ against the body wall, and*

*fixing the hollow organ by adjusting the tension on said filament outside the body.*

*13. The method of claim 12 wherein said retaining device comprises a head that extends cross-wise to said filament in a "T" arrangement upon release within the hollow organ.*

*14. A percutaneous fixation device suitable to fix the position of a hollow organ within a body which comprises*

*a tension filament having a distal end destined for the interior of the organ and a trailing portion extending in usage through an adjacent wall of the body and terminating outside the exterior of the body,*

*a cross bar attached to the distal end of said filament so as to form a "T" head for forcible engagement of the inner surface of the organ, and*

*a fastener connected to said filament for securing the trailing portion of said filament on the exterior of the body under tension so as to draw the organ toward the adjacent wall.*

*15. The device of claim 14, wherein said fastener comprises means for bearing against the exterior of the body.*

*16. The device of claim 15, wherein said fastener further comprises means for fixing the position of said bearing means along the trailing end of said filament.*

*17. A method of securing a hollow organ within a body to a wall of the body in preparation for insertion of a catheter through the wall into the interior of the organ, comprising the steps of*

*selecting a site for catheter insertion on the exterior of the body,*

*inserting a first retaining device from outside the body through the body wall into the hollow organ at a position on the exterior of the body nearby but displaced from said catheter insertion site, said retaining device having a head portion adapted to forcibly engage an interior wall of the hollow organ and a trailing tension filament attached to said head portion extending through the organ and body walls outside of the body,*

*pulling the trailing filament from outside the body to draw said retaining device against the interior wall of the hollow organ to pull the hollow organ against the body wall,*

*fixing the hollow organ by adjusting the tension on said filament outside the body, and*

*repeating the steps of inserting, pulling and fixing with a plurality of similar retaining devices at other positions, said other positions together with the position of said first retaining device surrounding said catheter insertion site.*

*18. The method of claim 17, wherein four of said retaining devices are used in a square configuration centered on said catheter insertion site.*

*19. A method for the fixation of a hollow organ of a living body to a body wall comprising:*

*percutaneously providing a tract from outside the body through the skin and into the hollow organ,*

*inserting a retaining device attached to a trailing tension filament, through the tract from outside the body, into said hollow organ in the manner that a portion of said trailing tension filament remains outside of the body,*

*said retaining device having a portion adapted to engage and apply pressure to an interior wall of said hollow organ,*

*releasing said retaining device within said hollow organ from said tract,*

*pulling a portion of said trailing tension filament from outside the body to draw said retaining device against the interior wall of said hollow organ to pull said organ against the body wall, and*

*fixing said organ by adjusting the tension on said filament.*

* * * * *